United States Patent [19]

Howard et al.

[11] Patent Number: 5,661,563
[45] Date of Patent: Aug. 26, 1997

[54] REFLECTANCE SPECTROSCOPE WITH READ HEAD FOR MINIMIZING SINGLY-REFLECTED LIGHT RAYS

[75] Inventors: Willis Howard; Gerald H. Shaffer, both of Elkhart, Ind.

[73] Assignee: Bayer Corporation, Elkhart, Ind.

[21] Appl. No.: 647,122

[22] Filed: May 9, 1996

[51] Int. Cl.⁶ .................................................. G01N 21/47
[52] U.S. Cl. ...................................... 356/446; 356/402
[58] Field of Search ................................... 356/402, 446, 356/445

[56] References Cited

U.S. PATENT DOCUMENTS

| | | | |
|---|---|---|---|
| 4,755,058 | 7/1988 | Shaffer | 356/408 |
| 5,028,139 | 7/1991 | Kramer et al. | 356/446 |
| 5,165,078 | 11/1992 | Hough et al. | 359/233 |
| 5,518,689 | 5/1996 | Dosmann et al. | 356/446 |

*Primary Examiner*—F. L. Evans
*Attorney, Agent, or Firm*—Roger N. Coe

[57] ABSTRACT

A reflectance spectroscope, which is provided with one or more optical paths which prevent substantially all singly reflected light rays from reaching the intended destination (s), is provided with a source of illumination for generating light rays, a support member adapted to support a reagent pad, the support member having a position in which the reagent pad is illuminated by the light rays generated by the illumination source, a reflectance detector positioned to receive light rays from the reagent pad, and means for defining an optical path in which substantially all singly-reflected light rays are prevented from reaching the intended destination. The optical path may be between the illumination source and the reagent pad, or between the reagent pad and the area in which the detector is provided.

18 Claims, 2 Drawing Sheets

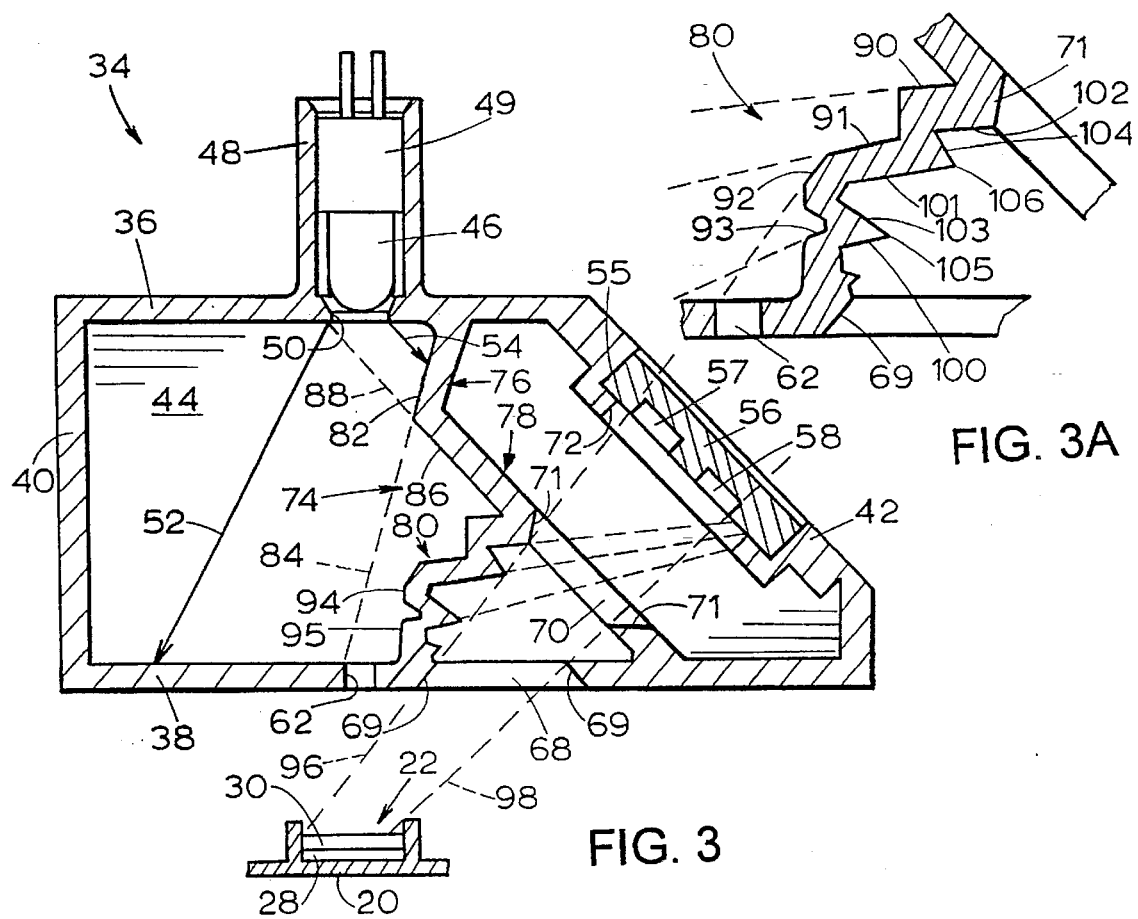
FIG. 3A
FIG. 3
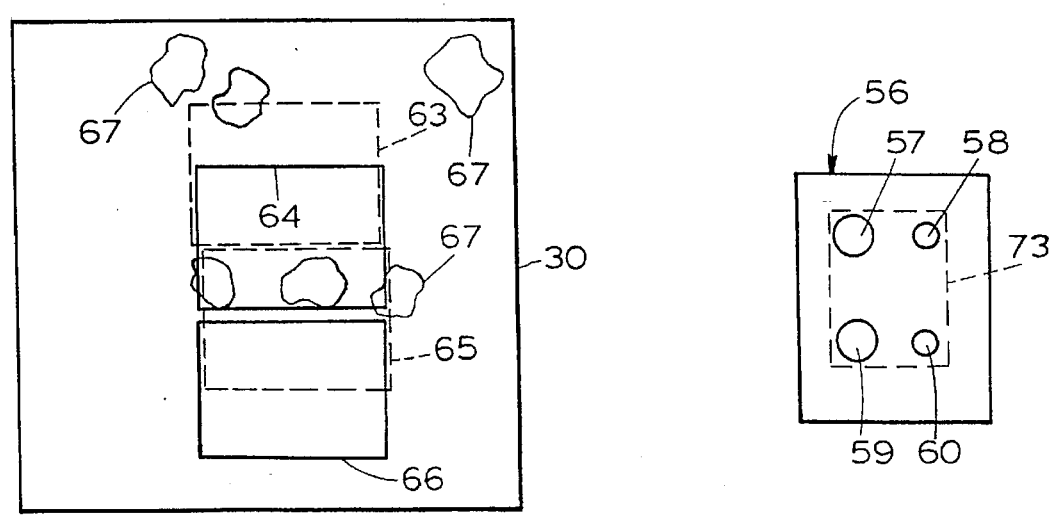
FIG. 5
FIG. 4 ns\n
REFLECTANCE SPECTROSCOPE WITH READ HEAD FOR MINIMIZING SINGLY-REFLECTED LIGHT RAYS

BACKGROUND OF THE INVENTION

The present invention relates to a spectroscope for performing tests on a sample of body fluid to be analyzed, and more particularly to a reflectance spectroscope having a read head for minimizing singly-reflected light rays.

It is useful for various medical diagnostic purposes to utilize a reflectance spectroscope to analyze samples of body fluid, for example, to detect on immunotest strips or chemistry test strips the presence of blood in a person's urine. Conventional reflectance spectroscopes have been used to detect the presence of blood in a urine sample disposed on a reagent pad. Any blood present in the urine reacts with the reagent on the reagent pad, causing the reagent pad to change color to an extent which depends on the concentration of the blood. For example, in the presence of a relatively large concentration of blood, such a reagent pad may change in color from yellow to dark green.

One conventional reflectance spectroscope detects the concentration of the blood by illuminating the reagent pad and detecting, via a conventional reflectance detector, the amount of light received from the reagent pad, which is related to the color of the reagent pad. Based upon the magnitude of the reflectance signal generated by the reflectance detector, the spectroscope assigns the urine sample to one of a number of categories, e.g. a first category corresponding to no blood, a second category corresponding to a small blood concentration, a third category corresponding to a medium blood concentration, and a fourth category corresponding to a large blood concentration.

A prior art reflectance spectroscope has been provided with an optical system in the form of a read head in which a light bulb is disposed directly above the reagent pad to be tested and a reflectance detector is disposed at a 45° angle to the horizontal surface of the reagent pad. Light from that spectroscope passes through a first vertical optical path from the illumination source to the reagent pad and through a second optical path, disposed 45° with respect to the first optical path, from the reagent pad to the reflectance detector.

One problem with conventional reflectance spectroscopes is that light rays can be reflected from internal surfaces of the read head so that they are scattered in unintended directions, thus adversely affecting the accuracy of the spectroscope. Such unintended scattering of light rays may cause the reagent pad to be illuminated non-uniformly; it may cause areas adjacent the reagent pad to be illuminated which are not intended to be illuminated; and it may distort the distribution of light received by the reflectance detector from the reagent pad, thus adversely effecting the accuracy of the spectroscope.

SUMMARY OF THE INVENTION

The present invention is directed to a reflectance spectroscope with an optical illumination system that is designed with one or more optical paths which prevent substantially all singly reflected light rays from reaching the intended destination. The inventors have recognized that it is desirable, to obtain maximum accuracy for the spectroscope, to have light rays illuminate a reagent pad directly from an illumination source without reflection, and to have light rays from the reagent pad reach the detection area directly without reflection.

A reflectance spectroscope in accordance with the invention has a source of illumination for generating light rays, a support member adapted to support a reagent pad, the support member having a position in which the reagent pad is illuminated by the light rays generated by the illumination source, a reflectance detector positioned to receive light rays from the reagent pad, and means for defining an optical path in which substantially all singly-reflected light rays are prevented from reaching the intended destination.

Where the optical path is between the illumination source and the reagent pad, the spectrometer may be provided with a housing having an aperture formed therein, the aperture being disposed between the illumination source and the reagent pad and being adapted to cause the light rays generated by the illumination source to illuminate an area of the reagent pad.

The means for defining the optical path may have a non-planar wall portion comprising a first wall portion with a specular reflective surface disposed to reflect substantially all of the light rays generated by the illumination source which reach the first wall portion to an area which does not include the aperture, and a second wall portion with a specular reflective surface disposed to reflect substantially all of the light rays generated by the illumination source which reach the second wall portion to an area which does not include the aperture.

Where the optical path is between the reagent pad and the detection area, the spectrometer may be provided with a non-planar wall portion comprising a first wall portion with a specular reflective surface disposed to reflect substantially all of the light rays which reach the first wall portion from the reagent pad to an area which does not include the detection area, and a second wall portion with a specular reflective surface disposed to reflect substantially all of the light rays which reach the second wall portion from the reagent pad to an area which does not include the detection area.

These and other features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 3 is a cross-sectional view of a read head used in the spectroscope;

FIG. 3A is an enlarged view of a portion of the read head shown in FIG. 3;

FIG. 4 is a schematic view of a detector array used in the spectroscope; and

FIG. 5 is an enlarged view of a reagent pad and a number of illuminated areas on the reagent pad.

DETAILED DESCRIPTION OF A PREFERRED EMBODIMENT

Figure 1:
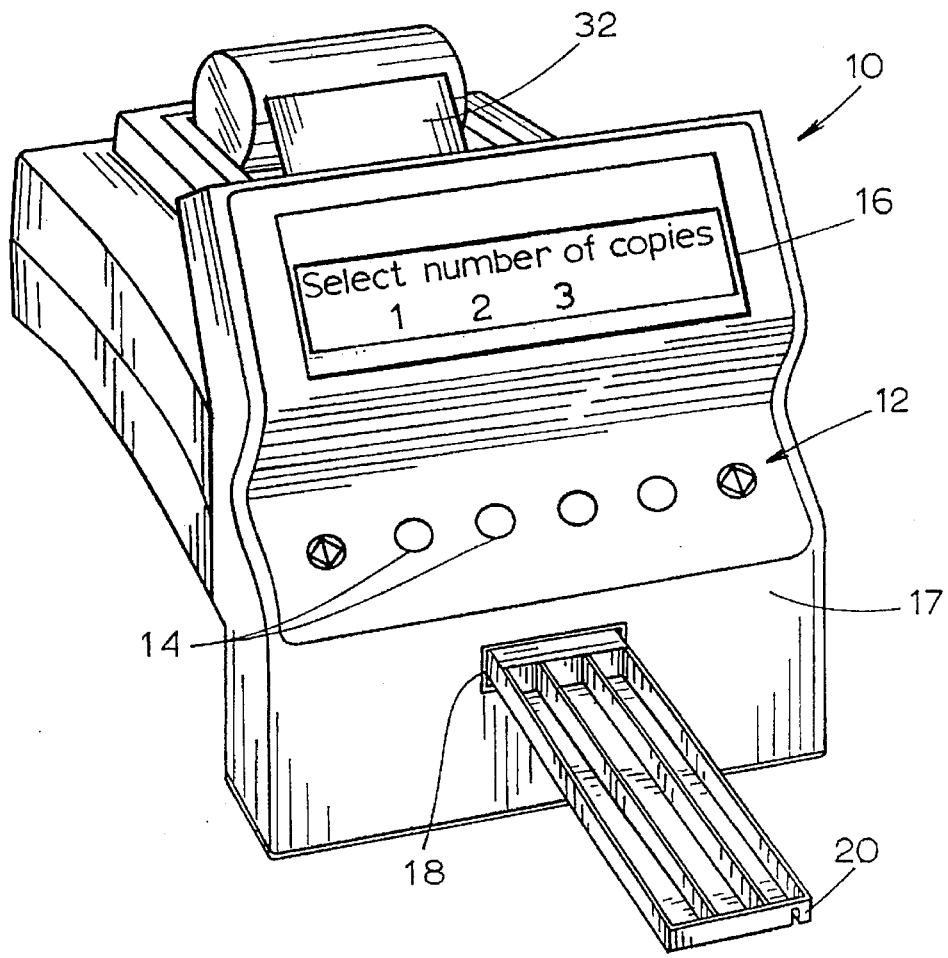
FIG. 1 is a perspective view of a reflectance spectroscope which may be used to perform various tests of a body fluid sample disposed on a reagent strip.
Figure 2:
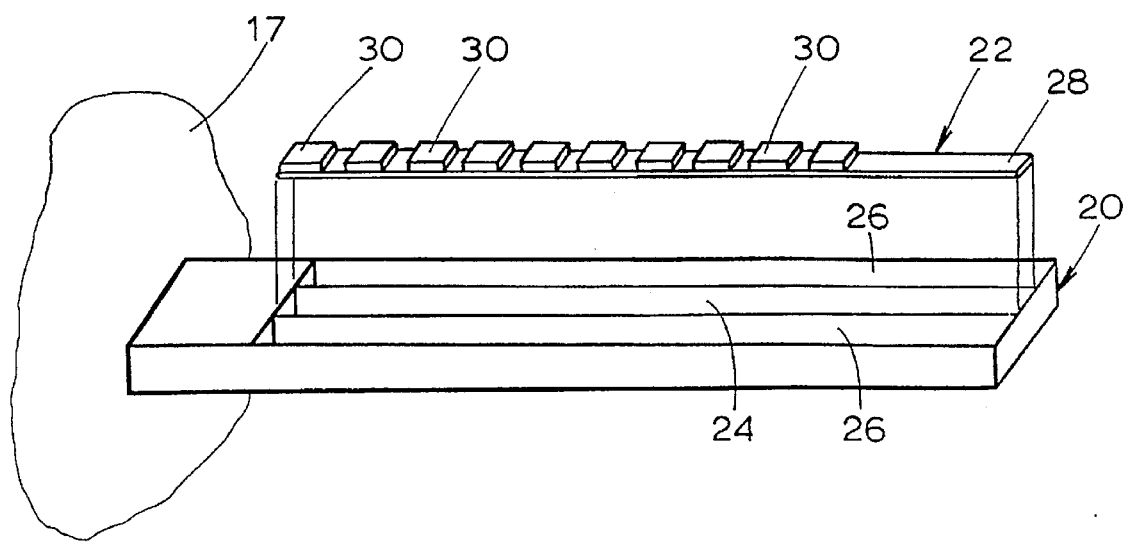
FIG. 2 is a perspective view of a reagent strip and a reagent tray used with the spectroscope of FIG. 1.

FIG. 1 illustrates a reflectance spectroscope 10 for performing various tests, such as urinalysis tests, on a reagent strip. The spectroscope 10 has an integral keyboard 12 with a number of entry keys 14 that may be depressed by the user. A visual display 16 for displaying various messages relating to the operation of the spectroscope 10 is disposed above the keyboard 12. Referring to FIGS. 1 and 2, the spectroscope 10 has a front face 17 with an opening 18 formed therein in which a tray 20 for carrying a reagent strip 22 is retractably disposed. The tray 20 has a central channel 24 and two side channels 26 formed therein, and the central channel 24 is sized to conform to the shape of the reagent strip 22.

The reagent strip 22 has a thin, non-reactive substrate 28 on which a number of reagent pads 30 are fixed. Each reagent pad 30 is composed of a relatively absorbent material impregnated with a respective reagent, each reagent and reagent pad 30 being associated with a particular test to be performed. When urinalysis tests are performed, they may include, for example, a test for leukocytes in the urine, a test of the pH of the urine, a test for blood in the urine, etc. When each reagent pad 30 comes into contact with a urine sample, the pad changes color over a time period, depending on the reagent used and the characteristics of the urine sample. The reagent strip 22 may be, for example, a Multistix® reagent strip commercially available from Bayer Corporation.

To perform urinalysis testing, the reagent strip 22 is dipped into a urine sample to be tested so that all of the reagent pads 30 are immersed in the sample. After the side of the reagent strip 22 is blotted to remove excess urine, the strip 22 is placed in the central channel 24 of the tray 20, and after the user presses one of the start keys 14 to initiate testing, the tray 20 is automatically retracted into the spectroscope 10.

A respective test is performed on each of the reagent pads 30 by illuminating a portion of the reagent pad 30 with white light from a light source and then determining the color of the reagent pad 30 based upon detection of light received from the illuminated portion of the reagent pad 30 at an angle (e.g. 45°) from the upper surface of the pad 30. After each test is performed, the tray 20 is repositioned relative to the light source so that the next reagent pad 30 to be tested is illuminated. When the testing is completed, the spectroscope 10 generates a record of the results, which are displayed on the display 16 and/or printed on a strip of paper 32 via a printer and/or sent to a computer.

FIG. 3 is a cross-sectional view of an optical system, in the form of a read head 34, for illuminating portions of the reagent pads 30 and for detecting light from the reagent pads 30, and a portion of the tray 20 on which the reagent strip 22 is disposed. Referring to FIG. 3, the read head 34 has a housing with a top wall 36, a bottom wall 38, a side wall 40, an angled wall 42, a planar back wall 44, and a planar front wall (not shown) parallel to the back wall 44. An illumination source in the form of a light bulb 46 is supported directly above the reagent pad 30 to be tested via a cylindrical housing portion 48 integrally formed with the top wall 36.

The lower spherical portion of the light bulb 46 has a concentrating lens integrally formed therein, and the lower spherical surface is acid-etched to provide it with an uneven, diffusing surface so that the shape of the bulb filament does not contribute to non-uniformity of the emitted light. When manufactured, the bulb 46 is dynamically fitted to a ceramic base 49 when the bulb 46 is illuminated to ensure that the axial direction in which bulb 46 emits light is substantially parallel to the longitudinal axis of the ceramic base 49. The bulb 46 emits light through a circular aperture 50 formed in the top wall 36 to form a cone of light defined by a first edge ray 52 and a second edge ray 54.

The angled side wall 42 has a rectangular aperture 55 formed therein in which a rectangular detector array 56 is disposed. The detector array 56 has four reflectance detectors 57, 58, 59, 60 disposed therein (see FIG. 4), each of which is composed of a conventional colored or IR filter and a conventional silicon detector. Each filter allows light having a distinct wavelength to pass through so that each of the detectors 57–60 is responsive to light of a different wavelength range. The four wavelength bands of the filters are: 400–510 nm (nanometers) (blue); 511–586 nm (green); 587–660 nm (red); and 825–855 nm (infrared). Depending on the type of test being performed, one or more of the detectors 57–60 may be used.

Light passes through a first optical path from the light bulb 46, through a relatively small rectangular aperture 62 formed in the bottom wall 38, to illuminate a relatively small rectangular area of the reagent pad 30 being tested. The reagent pad 30 may be moved relative to the aperture 62 so that different rectangular areas of the reagent pad 30 are illuminated.

Referring to FIG. 5, the illuminated areas may include a first area indicated by a dotted box 63, a second area indicated by a solid box 64, a third area indicated by a dotted box 65, and a fourth area indicated by a solid box 66. Although shown slightly vertically offset in FIG. 5 so that each box can be distinctly seen, the illuminated areas 63–66 are linearly offset with respect to each other, and adjacent areas partially overlap each other. A number of irregularly shaped areas 67 representing non-hemolyzed blood cell fragments are also shown in FIG. 5.

Light passes through a second optical path from the illuminated area on the reagent pad 30, through a first rectangular detection aperture 68 having angled edges 69 formed in the bottom wall 38, through a second rectangular detection aperture 70 having angled edges 71, and through a rectangular aperture 72 formed in the angled wall 42 to a detection area 73 (FIG. 4) in which the four detectors 57–60 are disposed.

The interior of the read head 34 is provided with an irregularly shaped baffle 74 composed of a first planar wall segment 76, a second planar wall segment 78, and a zig-zag shaped wall segment 80. The shape of the baffle 74 is designed to prevent singly-reflected light rays from reaching the reagent pad 30 from the light bulb 46 and to prevent singly-reflected light rays from reaching the detector area 73 from the reagent pad 30.

All surfaces of the baffle 74 and all interior surfaces of the housing walls 36, 38, 40, 42, 44 are shiny, specular surfaces so that any light incident upon any surface at an angle of incidence is reflected from that surface at an angle of reflection equal to the angle of incidence. This may be accomplished by injection-molding the read head 34 from a metal mold having highly polished molding surfaces. The read head 34 is preferably formed of black plastic so that only a small percentage of light, e.g. 5%, incident upon any of its internal surfaces is reflected. Consequently, any light that undergoes at least two reflections from any interior surfaces of the read head 34 is attenuated by at least 99.75%.

Referring to FIG. 3, the wall segment 76 has a specular surface 82 that is angled in a direction indicated by a dotted line 84, which intersects the bottom wall 38 at a point just to the left of the aperture 62. Consequently, any light rays emitted by the bulb 46 that impinge upon the surface 82 are reflected to an area to the left of the aperture 62. It should be noted that any such rays are reflected at least twice (in actuality at least three times) before they can pass through the aperture 62. It should also be noted that no light can be reflected from the surface 82 and pass directly through the aperture 62 without further reflection since the surface 82 is not visible when the interior of the read head 34 is viewed from the aperture 62.

The wall segment 78 has a specular surface 86 angled in a direction indicated by a dotted line 88, which intersects the top wall 36 at a point to the left of the circular opening 50 through which light passes. Consequently, there is no direct path from the light bulb 46 to the surface 86; therefore, any light that is reflected from the surface 86 to the aperture 62 will have undergone at least two (more than two in actuality) reflections from the interior surfaces of the read head 34.

FIG. 3A is an enlarged view of a portion of read head 34 shown in FIG. 3. Referring to FIGS. 3 and 3A, the zig-zag wall segment 80 has angled surfaces 90–93, each of which is angled in a direction indicated by a respective dotted line. Since all of the dotted lines intersect the bottom wall 38 or the side wall 40 to the left of the aperture 62, no light that impinges upon these surfaces 90–93 directly from the light bulb 46 can be reflected directly to the aperture 62. The zig-zag wall segment 80 has two further surfaces 94, 95 (FIG. 3) that are angled so that any light that impinges on those surfaces directly from the bulb 46 is reflected exclusively to the area of the bottom wall 38 to the right side of the aperture 62.

The only surfaces from which light rays emitted by the bulb 46 can be singly-reflected and still pass through the aperture 62 are the vertical walls of the aperture 62 itself. However, such singly-reflected light rays constitute an insignificant amount of the total light which passes directly from the light bulb 46 to the reagent pad 30 without reflection. There is also a singly-reflected light path from the bulb 46 to the walls 40 or 44 to the aperture 62. But because the bulb 46 concentrates light in a forward direction within the cone defined by rays 52 and 54, the amount of light going through the aperture 62 from this path is insignificant.

The second optical path, from the reagent pad 30 to the detector area 73 (FIG. 4), is generally indicated by a pair of dotted lines 96, 98. The side of the zig-zag wall segment 80 which is disposed adjacent the second optical path has a plurality of planar, specular surfaces 100, 101, 102 which are angled in a direction indicated by a number of corresponding dotted lines (shown in FIG. 3) which intersect the angled side wall 42 at a point to the lower right of the detector area 73. Consequently, any light rays that impinge upon these surfaces 100–102 directly from the reagent pad 30 without reflection cannot reach the detector area 73 without at least one more reflection, and thus any such light rays will be attenuated by at least 99.75%.

The side of the zig-zag wall segment 80 which is disposed adjacent the second optical path has a plurality of planar, specular surfaces 103, 104 (FIG. 3A) which are angled so that no light rays from the reagent pad 30 can reach the surfaces 103, 104 directly without at least one reflection. Consequently, any light rays that impinge upon these surfaces 103–104 will already have undergone at least one reflection, and therefore any such light rays that eventually reach the detector area 73 will be reflected at least twice and thus be attenuated by at least 99.75%.

The wall surfaces 100 and 103 join at an edge 105, and the wall surfaces 101 and 104 join at an edge 106, the edges 105, 106 being substantially aligned with a respective edge of the detection area 73, and the edges 69, 71 of the detection apertures 68, 70 are aligned with the edges of the detection area 73.

The configuration of the read head allows the read head to be made very small while maintaining small height sensitivity. Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed and sought to be secured by Letters Patent of the United States is:

1. A reflectance spectroscope, comprising:

a source of illumination for generating light rays;

a support member adapted to support a reagent pad, said support member having a position in which said reagent pad is illuminated by said light rays generated by said illumination source;

a reflectance detector positioned to receive light rays from said reagent pad, said reflectance detector occupying a detection area;

a housing having an aperture formed therein, said aperture being disposed between said illumination source and said reagent pad and being adapted to cause said light rays generated by said illumination source to illuminate an area of said reagent pad;

means for defining a first optical path from said illumination source to said reagent pad in which substantially all singly-reflected light rays generated by said illumination source are prevented from reaching said reagent pad, said means for defining said first optical path having a non-planar wall comprising:

a first wall portion with a specular reflective surface disposed to reflect substantially all of said light-rays generated by said illumination source which reach said first wall portion to an area which does not include said aperture; and a second wall portion with a specular reflective surface disposed to reflect substantially all of said light rays generated by said illumination source which reach said second wall portion to an area which does not include said aperture; and means for defining a second optical path from said reagent pad to said reflectance detector in which substantially all singly-reflected light rays from said reagent pad are prevented from reaching said reflectance detector, said means for defining said second optical path having a non-planar wall comprising:

a third wall portion with a specular reflective surface disposed to reflect substantially all of said light rays which reach said third wall portion from said reagent pad to an area which does not include said detection area; and a fourth wall portion with a specular reflective surface disposed to reflect substantially all of said light rays which reach said fourth wall portion from said reagent pad to an area which does not include said detection area.

2. A reflectance spectroscope as defined in claim 1 wherein at least one of said wall portions is substantially planar.

3. A reflectance spectroscope as defined in claim 1 wherein all of said wall portions are substantially planar.

4. A reflectance spectroscope as defined in claim 1 wherein said housing has a detection aperture formed therein, said detection aperture being disposed between said reagent pad and said reflectance detector.

5. A reflectance spectroscope as defined in claim 4 wherein said means for defining said second optical path comprises at least one edge defined by a pair of wall portions, said edge being substantially aligned with an edge of said detection area and an edge of said detection aperture.

6. A reflectance spectroscope as defined in claim 1 wherein said housing has a first detection aperture formed therein, said first detection aperture having a first edge and a second edge and being disposed between said reagent pad and said reflectance detector so that said edges of said first detection aperture are substantially aligned with a pair of edges of said detection area.

7. A reflectance spectroscope as defined in claim 6 wherein said housing has a second detection aperture formed therein, said second detection aperture having a first edge and a second edge and being disposed between said first detection aperture and said reflectance detector so that said edges of said second detection aperture are substantially aligned with said pair of edges of said detection area.

8. A reflectance spectroscope, comprising:

a source of illumination for generating light rays;

a support member adapted support a reagent pad, said support member having a position in which said reagent pad is illuminated by said light rays generated by said illumination source;

a reflectance detector positioned to receive light rays from said reagent pad; and means for defining a first optical path from said illumination source to said reagent pad in which substantially all singly-reflected light rays generated by said illumination source are prevented from reaching said reagent pad.

9. A reflectance spectroscope as defined in claim 8 additionally comprising a housing having an aperture formed therein, said aperture being disposed between said illumination source and said reagent pad and being adapted to cause said light rays generated by said illumination source to illuminate an area of said reagent pad.

10. A reflectance spectroscope as defined in claim 9 wherein said means for defining a first optical path has a non-planar wall portion comprising:

a first wall portion with a specular reflective surface disposed to reflect substantially all of said light rays generated by said illumination source which reach said first wall portion to an area which does not include said aperture; and a second wall portion with a specular reflective surface disposed to reflect substantially all of said light rays generated by said illumination source which reach said second wall portion to an area which does not include said aperture.

11. A reflectance spectroscope as defined in claim 10 wherein at least one of said first and second wall portions is substantially planar.

12. A reflectance spectroscope as defined in claim 8 additionally comprising means for defining a second optical path from said reagent pad to said reflectance detector in which substantially all singly-reflected light rays from said reagent pad are prevented from reaching said reflectance detector.

13. A reflectance spectroscope as defined in claim 12 wherein said reflectance detector occupies a detection area and wherein said reflectance spectroscope additionally comprises a housing.

14. A reflectance spectroscope as defined in claim 13 wherein said means for defining a second optical path has a non-planar wall portion comprising:

a first wall portion with a specular reflective surface disposed to reflect substantially all of said light rays which reach said first wall portion from said reagent pad to an area which does not include said detection area; and a second wall portion with a specular reflective surface disposed to reflect substantially all of said light rays which reach said second wall portion from said reagent pad to an area which does not include said detection area.

15. A reflectance spectroscope, comprising:

a source of illumination for generating light rays;

a support member adapted to support a reagent pad, said support member having a position in which said reagent pad is illuminated by said light rays generated by said illumination source;

a reflectance detector positioned to receive light rays from said reagent pad; and means for defining a first optical path from said reagent pad to said reflectance detentor in which substantially all singly-reflected light rays from said reagent pad are prevented from reaching said reflectance detector.

16. A reflectance spectroscope as defined in claim 15 wherein said reflectance detector occupies a detection area and wherein said reflectance spectroscope additionally comprises a housing.

17. A reflectance spectroscope as defined in claim 16 wherein said means for defining a first optical path has a non-planar wall portion comprising:

a first wall portion with a specular reflective surface disposed to reflect substantially all of said light rays which reach said first wall portion from said reagent pad to an area which does not include said detection area; and a second wall portion with a specular reflective surface disposed to reflect substantially all of said light rays which reach said second wall portion from said reagent pad to an area which does not include said detection area.

18. A reflectance spectroscope as defined in claim 17 wherein at least one of said first and second wall portions is substantially planar.

* * * * *